United States Patent
Nagata et al.

(10) Patent No.: US 11,690,768 B2
(45) Date of Patent: Jul. 4, 2023

(54) SYSTEMS AND METHODS FOR COMMUNICATION BETWEEN WHEELCHAIRS AND VEHICLES

(71) Applicant: Toyota Motor North America, Inc., Plano, TX (US)

(72) Inventors: Katsumi Nagata, Foster City, CA (US); Stephen McFarland, Jr., Allen, TX (US); Jerry R. Tipper, Plano, TX (US)

(73) Assignee: Toyota Motor North America, Inc., Plano, TX (US)

( * ) Notice: Subject to any disclaimer, the term of this patent is extended or adjusted under 35 U.S.C. 154(b) by 577 days.

(21) Appl. No.: 16/809,680

(22) Filed: Mar. 5, 2020

(65) Prior Publication Data
US 2021/0275368 A1 Sep. 9, 2021

(51) Int. Cl.
*A61G 3/08* (2006.01)
*B60N 2/02* (2006.01)
(Continued)

(52) U.S. Cl.
CPC .......... *A61G 3/0808* (2013.01); *A61B 5/1171* (2016.02); *A61G 5/04* (2013.01); *B60N 2/0244* (2013.01); *A61G 2205/60* (2013.01)

(58) Field of Classification Search
None
See application file for complete search history.

(56) References Cited

U.S. PATENT DOCUMENTS

| 5,137,413 A * | 8/1992 | Ressler | B60P 1/43 280/43.11 |
| 8,519,824 B1 * | 8/2013 | Rankin | B64D 11/00 244/118.5 |

(Continued)

FOREIGN PATENT DOCUMENTS

| JP | 2006142855 A | 6/2006 |
| KR | 101305336 B1 | 9/2013 |

(Continued)

OTHER PUBLICATIONS

Saripalli, S., "Are self-driving cars the future of mobility for disabled people?", Oct. 6, 2017; URL: http://theconversation.com/are-self-driving-cars-the-future-of-mobility-for-disabled-people-84037 3 Pages.

(Continued)

*Primary Examiner* — Hunter B Lonsberry
*Assistant Examiner* — Daniel L Greene
(74) *Attorney, Agent, or Firm* — Dinsmore & Shohl LLP

(57) ABSTRACT

Embodiments herein are directed to a vehicle. The vehicle includes a passenger compartment and a master controller. The passenger compartment has a plurality of rear passenger seats disposed on a track. Each seat of the plurality of rear passenger seats is configured to move on the track. The master controller is configured to receive a first data from a wheelchair and to direct a movement of each seat of the plurality of rear passenger seats along the track. In response to receiving the first data, the master controller actuates at least one actuator to move at least one of the plurality of rear passenger seats along the track to provide a transportation space for the wheelchair based on the first data received from the wheelchair.

16 Claims, 9 Drawing Sheets

(51) Int. Cl.
*A61G 5/04* (2013.01)
*A61B 5/1171* (2016.01)

(56) References Cited

U.S. PATENT DOCUMENTS

| | | | |
|---|---|---|---|
| 9,868,359 B2 | 1/2018 | Huston et al. | |
| 10,182,952 B1 | 1/2019 | Nelson-Herron et al. | |
| 2003/0127261 A1* | 7/2003 | Borroni-Bird | B60G 7/003 180/65.1 |
| 2004/0124655 A1* | 7/2004 | Takenoshita | B60N 2/245 296/65.13 |
| 2006/0229770 A1 | 10/2006 | Strong | |
| 2008/0228358 A1* | 9/2008 | Wang | B60R 21/01512 701/49 |
| 2012/0086249 A1* | 4/2012 | Hotary | B60N 2/20 297/284.3 |
| 2012/0191491 A1* | 7/2012 | Choi | G06Q 10/02 705/13 |
| 2017/0320408 A1* | 11/2017 | Laird | B60N 2/06 |
| 2017/0355295 A1* | 12/2017 | Gutowitz | B60K 1/00 |
| 2018/0135987 A1* | 5/2018 | Evans | A61G 5/02 |
| 2019/0052637 A1* | 2/2019 | Dean | H04W 12/04 |
| 2019/0231619 A1* | 8/2019 | Moore | G16H 70/20 |
| 2020/0047643 A1* | 2/2020 | Ellis | B60N 2/686 |
| 2020/0104770 A1* | 4/2020 | Aich | G01C 21/3423 |
| 2020/0262326 A1* | 8/2020 | Honda | B60N 2/002 |
| 2021/0117871 A1* | 4/2021 | Mitra | H04W 4/40 |
| 2021/0125110 A1* | 4/2021 | Yamazaki | G08B 7/066 |

FOREIGN PATENT DOCUMENTS

| | | | |
|---|---|---|---|
| KR | 20140036549 A * | 3/2014 | B60L 50/50 |
| KR | 20180060435 A | 6/2018 | |
| WO | 2012042458 A1 | 4/2012 | |

OTHER PUBLICATIONS

Lopresti, E. F., et al., "Automatic transport and retrieval system for power wheelchairs", RESNA 28th Annual Conference, Accessed Date: Jun. 20, 2019, URL: https://www.resna.org/sites/default/files/legacy/conference/proceedings/20 05/Research/SM/LoPresti.html 7 Pages.

* cited by examiner

SYSTEMS AND METHODS FOR COMMUNICATION BETWEEN WHEELCHAIRS AND VEHICLES

TECHNICAL FIELD

The present disclosure generally relates to interface control systems and, more specifically, to interface control systems between vehicles and wheelchairs that coordinate motor and/or actuator controls of a seat assembly in the vehicle to match the requirements needed for the wheelchair.

BACKGROUND

Certain users of a powered wheelchair may also be users of transportation vehicles, such as vans, buses, and the like. The transportation vehicles are generally configured with a passenger compartment having a plurality of seats, including both a driver seat and passenger seats, and at least one wheelchair transportation space configured for the user on the wheelchair to position the wheelchair while being transported by the transportation vehicle. The transportation vehicle may be further equipped with wheelchair ramps. Typically, the user in the wheelchair may use the ramp to board the transportation vehicle and then position the wheelchair in an available wheelchair transportation space, regardless of the size of the space, the location of the space, the other passengers, and the like. However, the transportation vehicle does not interface with the wheelchair to meet the needs of the user or the requirements of the wheelchair by automatically arranging the plurality of seats of the transportation vehicle based on the needs of the user or the requirements of the wheelchair.

SUMMARY

In one embodiment, a vehicle is provided. The vehicle includes a passenger compartment and a master controller. The passenger compartment has a plurality of rear passenger seats disposed on a floor surface. Each seat of the plurality of rear passenger seats is configured to move on and with respect to floor surface. The master controller is configured to receive a first data from a wheelchair and to direct a movement of each seat of the plurality of rear passenger seats along the track. In response to receiving the first data, the master controller actuates at least one actuator to move at least one of the plurality of rear passenger seats along the floor surface to provide a transportation space for the wheelchair based on the first data received from the wheelchair.

In another embodiment, a system having a vehicle is provided. The vehicle includes a passenger compartment and a master controller. The passenger compartment has a plurality of rear passenger seats and a floor. The floor includes a floor surface. Each seat of the plurality of rear passenger seats are communicatively coupled to the master controller. The master controller is configured to actuate at least one actuator to direct a movement of at least one seat of the plurality of rear passenger seats along the floor surface to a predetermined location within the passenger compartment such that a transportation space is provided for the wheelchair based on a first data transmitted to the master controller by the wheelchair.

In yet another embodiment, a method of communicating between a vehicle and a wheelchair is provided. The method includes receiving, by a master controller, an input from a user, the input corresponding to a request for transportation, receiving, by the master controller, a wheelchair requirement data or a user data from the wheelchair, determining, by the master controller, an optimal seat configuration of a plurality of rear passenger seats within the vehicle, and moving, by at least one actuator, at least one seat of the plurality of rear passenger seats into the optimal seat configuration based on the wheelchair requirement data or the user data.

These and additional objects and advantages provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
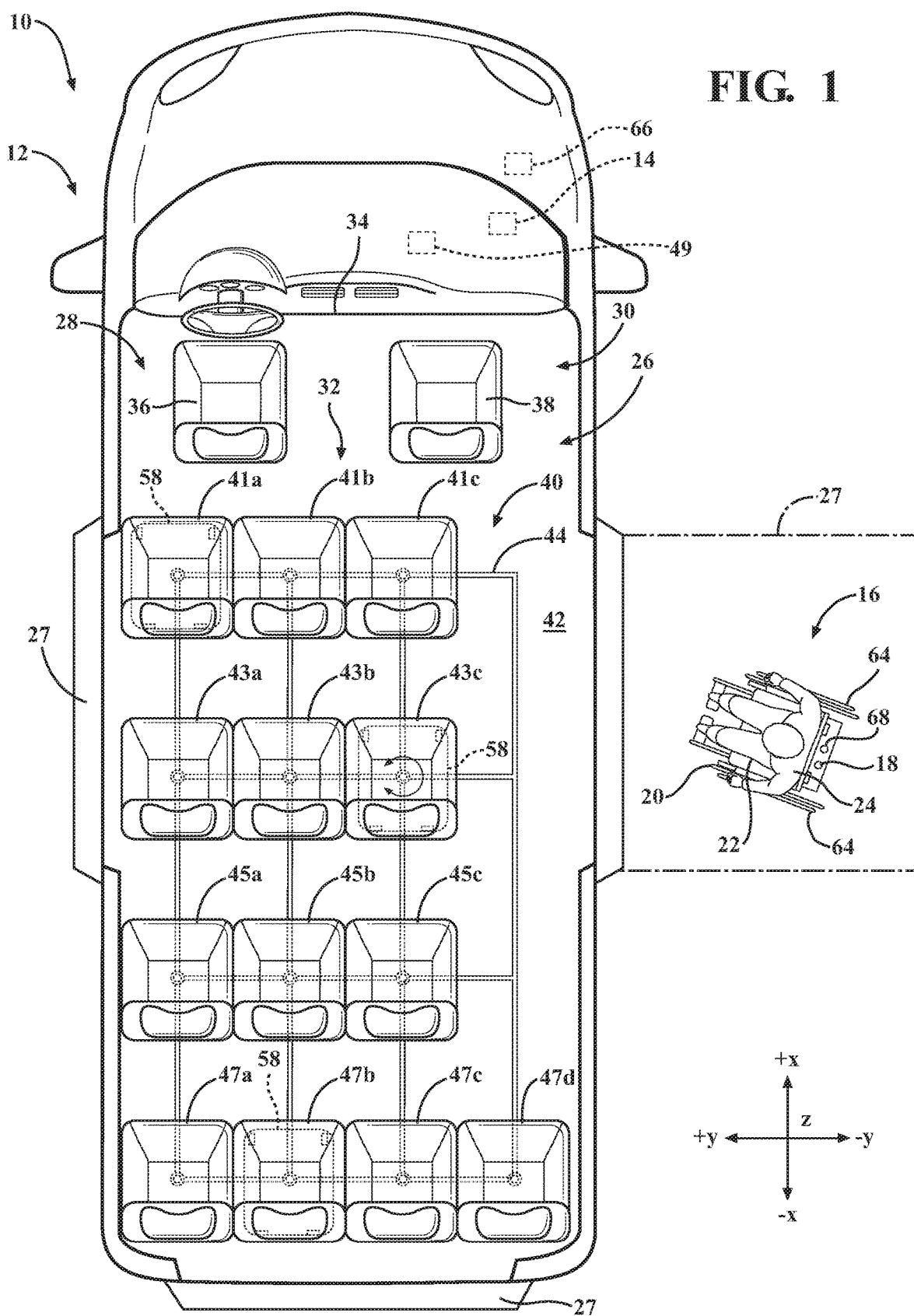
FIG. 1 schematically depicts a top down view of an illustrative system having a vehicle with a side mounted wheelchair ramp and a user on a wheelchair according to one or more embodiments shown or described herein.

The systems and methods described herein generally relate to an interface between a wheelchair and a vehicle that is configured to transport users and wheelchairs. The vehicle is configured to receive communications from the wheelchair and manipulate or move interior seating configurations, based on the communication from the wheelchair, to accommodate the wheelchair and/or the user. The vehicle may communicate with the wheelchair via Bluetooth, Wi-Fi, cellular frequencies and the like to communicatively couple a master controller of the vehicle with a control unit of the wheelchair to transmit data between them. The data transmitted between the vehicle and the wheelchair may be biometric ID, parameters for automatic vehicle seat adjustments, wheelchair battery state of charge, destination information, tasks to be performed after reaching the destination, special needs, and the like. The parameters for automatic vehicle seat adjustments may include user-specific variables such as weight, height, wheelchair requirements such as size, weight, wheelchair turning radius, and the like.

The vehicle is equipped to accept a wide variety of wheelchairs and may include, for example, trucks, vans, buses, cars, and the like. In some embodiments, the vehicle may be autonomous. In other embodiments, the vehicle may be purposed for rideshare accepting one or more wheelchairs. As such, the vehicle may be configured to accommodate multiple wheelchairs and non-wheelchair passengers.

As described in further detail herein, in operation, after receiving a communication from the control unit of the wheelchair, the vehicle prepares itself to load the wheelchair and user into the vehicle by automatically arranging the seats for loading and transport. The vehicle may require different wheelchair seating configurations based on vehicle design, the number of wheelchairs, wheelchair model, user-specific variables, and the like. In some embodiments, the vehicle may dynamically adjust the seats as a function of the passenger type, amount of passengers, ingress/egress location, (i.e., right, left, or rear side of the vehicle), and the like. During unloading, the reverse operation is used.

Further, in some embodiments, the vehicle may include a docking mechanism for the wheelchair that is configured to charge a battery of the wheelchair based on the transmitted data, for example, state of charge, destination, tasks after reaching the destination, and the like, such that the master controller of the vehicle determines a required reserve charge level for the wheelchair and delivers the charge. The reserve charge level calculation may incorporate terrain conditions at the destination that impact charging levels, (e.g., hill grade, regen opportunities, and the like). The charging rate may vary depending on the amount required (i.e., fast charging, normal charging, and maintenance charging). The docking mechanism is bidirectional such that the wheelchair may share its charge with the vehicle in case of a low vehicle charge condition.

In some embodiments, the master controller of the vehicle includes a scheduling feature where reservations may be cloud-based and incorporate variable loading/unloading times to maintain scheduled appointment times. The routes taken by the vehicle are modifiable in support of appointment timing.

As used herein, the term "communicatively coupled" means that coupled components are capable of exchanging data signals with one another such as, for example, electrical signals via conductive medium or a non-conductive medium, though networks such as via Wi-Fi, Bluetooth, and the like, electromagnetic signals via air, optical signals via optical waveguides, and the like.

As used herein, the term "system longitudinal direction" refers to the forward-rearward direction of the system (i.e., in a +/−X direction of the coordinate axes depicted in FIG. 1). The term "system lateral direction" refers to the cross-direction (i.e., along the Y axis of the coordinate axes depicted in FIG. 1), and is transverse to the longitudinal direction. The term "system vertical direction" refers to the upward-downward direction of the system (i.e., in the +/−Z-direction of the coordinate axes depicted in FIG. 1). As used herein, "upper" or "top" is defined as generally being towards the positive Z direction of the coordinate axes shown in the drawings. "Lower", "below" or "bottom" is defined as generally being towards the negative Z direction of the coordinate axes shown in the drawings.

Figure 2:
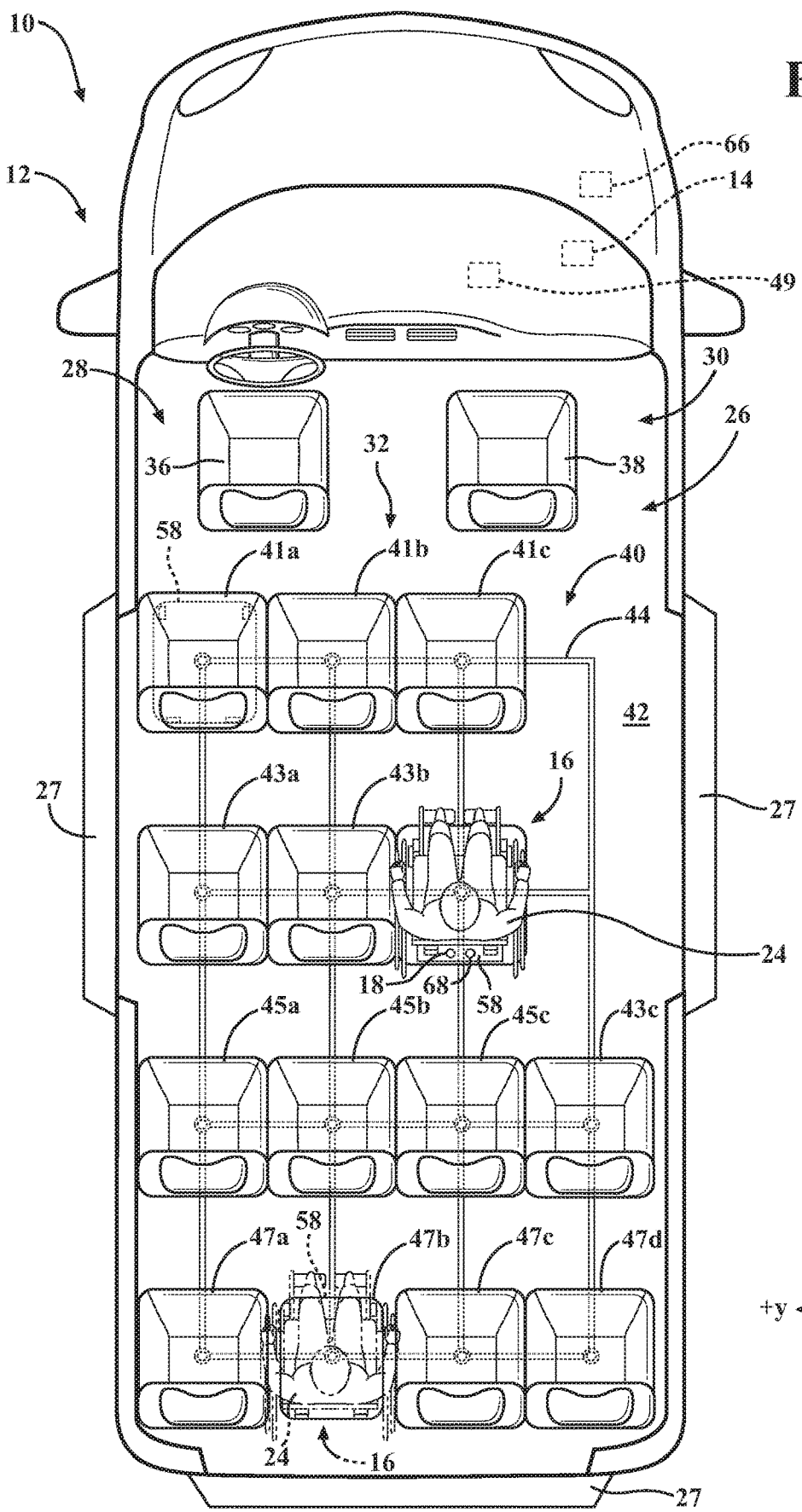
FIG. 2 schematically depicts the illustrative system of FIG. 1 with at least one seat of the vehicle moved to provide a wheelchair transportation space required for the user and the wheelchair to be positioned thereon within the vehicle according to one or more embodiments shown or described herein.

Referring initially to FIGS. 1-2, a schematic depiction of a system, generally designated 10, is provided. The system 10 generally includes an example vehicle 12 having a master controller 14 and a wheelchair 16 having a control unit 18. As described in greater detail herein, the system 10 may manipulate or move interior seating configurations of the example vehicle 12 based on communications between the control unit 18 of the wheelchair 16 and the master controller 14 of the example vehicle 12, to accommodate for the wheelchair requirements and/or user biometrics.

The wheelchair 16 is a generally recognized wheelchair that may include motorized components that allow a user to electronically control movement of the wheelchair. Accordingly, various components of the wheelchair 16 should be understood and are not described in further detail herein. In some embodiments, the wheelchair 16 may include a power base portion 20 and a seat 22 supported by the power base portion 20. Thus, the power base portion 20 is generally positioned below the seat 22 in a system vertical direction (i.e., positioned in the −Z direction of the coordinate axes of FIG. 1 relative to the seat 22). Still referring to FIGS. 1-2, in some embodiments, the power base portion 20 may raise, tilt, or otherwise move the seat 22. The seat 22 is generally configured to support a user 24 when the user 24 is seated in the wheelchair 16.

The example vehicle 12 includes a passenger compartment 26. Further, the example vehicle 12 includes at least one wheelchair ramp 27. The at least one wheelchair ramp 27 may be positioned along an exterior of the example vehicle 12 and provides access to the passenger compartment 26 by actuating into a lowered position, as illustrated by the dotted line in FIG. 1. The at least one wheelchair ramp 27 may be provided on either side of the example vehicle 12, a rear of the example vehicle 12, and/or a combination thereof. It should be appreciated that the actuation of the wheelchair ramp 25 may be by pneumatics, hydraulics, electrical, and the like.

The example vehicle 12 may be equipped to accept a wide variety of wheelchairs and may include, for example, trucks, vans, buses, cars, and the like. In some embodiments, the example vehicle 12 may be autonomous. In other embodiments, the example vehicle 12 may be purposed for rideshare accepting one or more wheelchairs. As such, the example vehicle 12 may be configured to accommodate multiple wheelchairs and non-wheelchair passengers.

The passenger compartment 26 includes a driver area 28, a front passenger area 30, and a rear passenger area 32. An instrument panel 34 is provided within the passenger compartment 26. The instrument panel 34 generally extends in the vehicle lateral direction (i.e., in the +/−Y direction) and includes, without limitation, an instrument cluster, a radio, and a climate control cluster including a plurality of individual vents. Further, the passenger compartment 26 includes a driver seat 36, a front passenger seat 38, and a plurality of rear passenger seats 40 positioned rearward of the driver seat 36 and the front passenger seat 38 in the vehicle longitudinal direction (i.e., in the +/−X direction).

The plurality of rear passenger seats 40 are arranged into four rows with a first row having a first row first seat 41a, a first row second seat 41b, and a first row third seat 41c, a second row having a second row first seat 43a, a second row second seat 43b, and a second row third seat 43c, a third row having a third row first seat 45a, a third row second seat 45b, and a third row third seat 45c, and a fourth row having a fourth row first seat 47a, a fourth row second seat 47b, a fourth row third seat 47c, and a fourth row fourth seat 47d. Located adjacent the driver seat 36 are the controls to the example vehicle 12 such as, without limitation, a steering wheel, a gas pedal, and a brake pedal.

In some embodiments, the passenger compartment 26 further includes a floor 42 that generally has a plurality of tracks 44 mounted therein. In other embodiments, the floor 42 includes actuators, magnets, and the like, below a floor surface 42a such that the floor surface 42a is smooth, or without tracks, grooves, and the like, as discussed in greater detail herein. In some embodiments, each of the plurality of tracks 44 are recessed into the floor 42. In other embodiments, portions of the plurality of tracks 44 are recessed into the floor 42 or include ramps to assist in the mobility of the wheelchair 16 to ride over them. The plurality of tracks 44 may be arranged in columns along the vehicle longitudinal direction (i.e., in the +/−X direction), in rows along the vehicle lateral direction (i.e., in the +/−Y direction) and/or a combination thereof, as illustrated in FIGS. 1 and 2. The plurality of tracks 44 may be a channel, a groove, a cavity formed between two sidewalls and the like. As such, it should be appreciated that a width of each track of the plurality of tracks 44 is less than an maximum outer side surface of a wheelchair wheel such that the wheelchair wheel will not fit within the channel, the groove, the cavity formed between two sidewalls, and the like of the plurality of tracks 44.

Figure 3A:
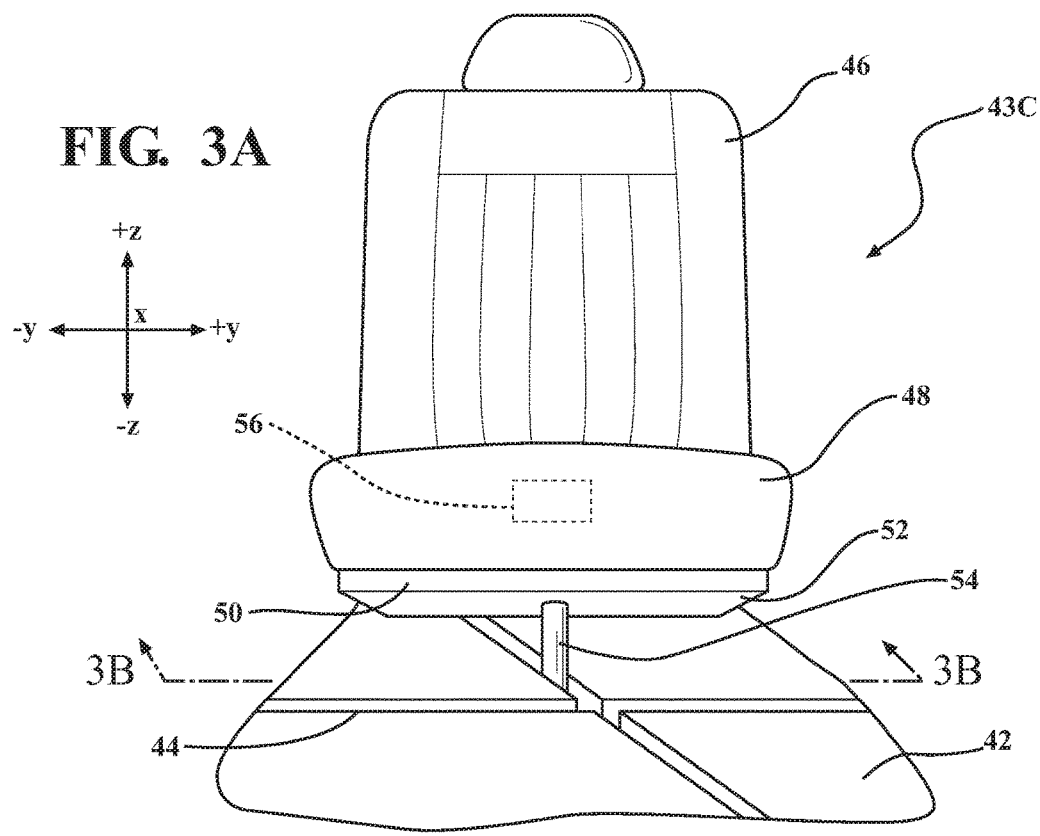
FIG. 3A schematically depicts an isolated view of a rear passenger seat engaged within a track of the illustrative system of FIG. 1 according to one or more embodiments shown or described herein.
Figure 3B:
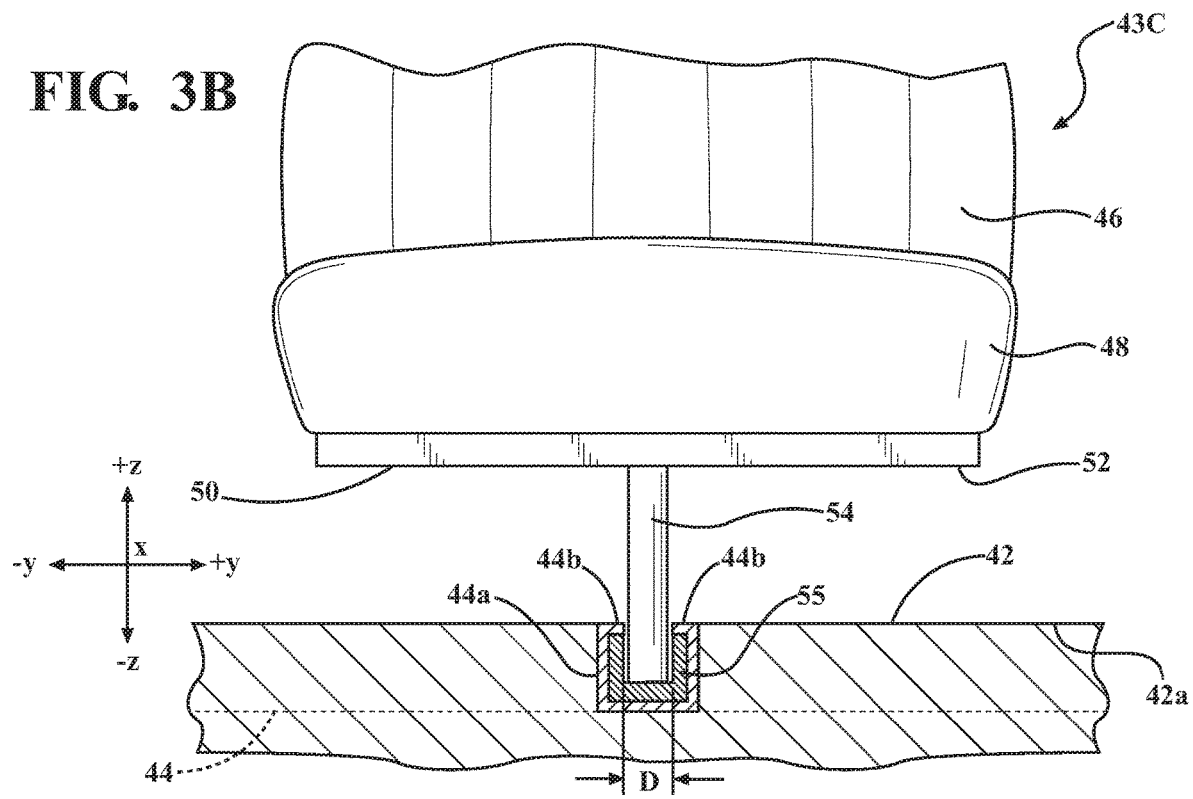
FIG. 3B schematically depicts a cross-sectional view of the rear passenger seat engaged within the track of FIG. 3A taken along line 3B-3B according to one or more embodiments shown or described herein.

Now referring to FIGS. 3A-3B, while still referring to FIGS. 1-2, each seat of the plurality of rear passenger seats 40, such as the second row third seat 43c, may include a seat back 46 and a seat cushion 48 coupled to a seat frame 50. The seat frame 50 includes a bottom surface 52. In some embodiments, at least one track engagement member 54 is positioned on the bottom surface 52 of a seat frame 50. Further, each seat of the plurality of rear passenger seats 40 may include at least one actuator 56 communicatively coupled to the master controller 14 of the example vehicle 12.

In this embodiment, a distal end of the at least one track engagement member 54 is configured to be received by, or within, the plurality of tracks 44. In some embodiments, the distal end of the at least one track engagement member 54 includes a retaining mechanism 55, such as a roller, a T-shape, and I-shape, or other mechanism to be received by and engages the plurality of tracks 44. In other embodiments, the distal end may be magnetic or electro-magnetic. The retaining mechanism 55 may be retained by a pair of sidewalls 44a that define the channel, the groove, and/or the cavity of the plurality of tracks 44. In some embodiments, each sidewall of the pair of sidewalls 44a includes a retaining surface 44b positioned at an upper surface the pair of sidewalls 44a to allow the at least one track engagement member 54 to move, but does not allow the retaining mechanism 55 of the at least one track engagement member 54 to release from the plurality of tracks 44. That is, the retaining mechanism 55 may engage with the pair of sidewalls 44a and/or the retaining surface 44b, to lock or retain the at least one track engagement member 54 into the channel, the groove, and/or the cavity of the plurality of tracks 44. As such, it should be appreciated that the distance D allows for the at least one track engagement member 54 to move within each track of the plurality of tracks 44, but does not allow the retaining mechanism 55 of the at least one track engagement member 54 to release the second row third seat 43c from the plurality of tracks 44.

It should be appreciated that, in some embodiments, the at least one track engagement member 54 may be positioned centered to the seat frame 50. In other embodiments, the at least one track engagement member 54 is offset from center on the seat frame 50. In yet other embodiments, the at least one track engagement member 54 includes two members positioned on each peripheral edge of the seat frame 50. In some embodiments, the track engagement member 54 may be removable from the seat frame 50, from the plurality of tracks 44, and the like such that each seat of the plurality of rear passenger seats 40, such as the second row third seat 43c, may be easily removed from the rear passenger compartment 32.

In this embodiment, the at least one actuator 56 is configured to provide movement to each seat of the plurality of rear passenger seats 40 to drive or move each seat along the plurality of tracks 44 via the at least one track engagement member 54 in a predetermined pattern. For example, the second row third seat 43c of the plurality of rear passenger seats 40 is depicted in the second row in FIG. 1 and has been automatically moved, via the at least one actuator 56 along the plurality of tracks 44, to the third row, as depicted in FIG. 2, and as discussed in greater detail herein.

In this embodiment, the at least one actuator 56 may receive commands from the master controller 14 of when to move at least one seat of the plurality of rear passenger seats 40, what predetermined pattern to follow, and the like, as discussed in greater detail herein. As such, in some embodiments, the at least one actuator 56 may be controllable by the master controller 14. The master controller 14 is not limited by this disclosure, and may generally any device that provides control signals to the at least one actuator 56 to cause the at least one actuator 56 to actuate. As such, the master controller 14 may be communicatively coupled to each one of the at least one actuator 56. In addition, in some embodiments, the plurality of rear passenger seats 40 may have a separate control unit or each seat of the plurality of rear passenger seats 40 may have independent control units that may be communicatively coupled to the master controller 14 such that each control unit may transmit/receive signals to/from the master controller 14.

In some embodiments, the at least one actuator 56 may be positioned within each one of the plurality of rear passenger seats 40, as depicted in FIG. 3, or may be positioned along the floor 42. In this embodiment, the tracks 44 may be energized to cause at least one seat of the plurality of rear passenger seats 40 to move. In other embodiments, the at least one seat of the plurality of rear passenger seats 40 may also be attached to an elongated member such as a rope, a chain, a rod, and the like, which is also coupled to the actuator such that the actuator may cause at least one seat of the plurality of rear passenger seats 40 to move via the elongated member.

In some embodiments, the passenger compartment 26 may further include at least one sensing device 49. The at least one sensing device 49 may be generally used to sense and/or to detect the current seating arrangement, the current passenger positions within each seat of the plurality of rear passenger seats 40, the current wheelchair and user positions, and the like. The at least one sensing device 49 may be configured to provide feedback during operation. More specifically, the at least one sensing device 49 may transmit a plurality of outputs, either wired or wirelessly, to the master controller 14 to provide data that is used to determine the optimal seating arrangement, as explained in greater detail herein.

Figure 4A:
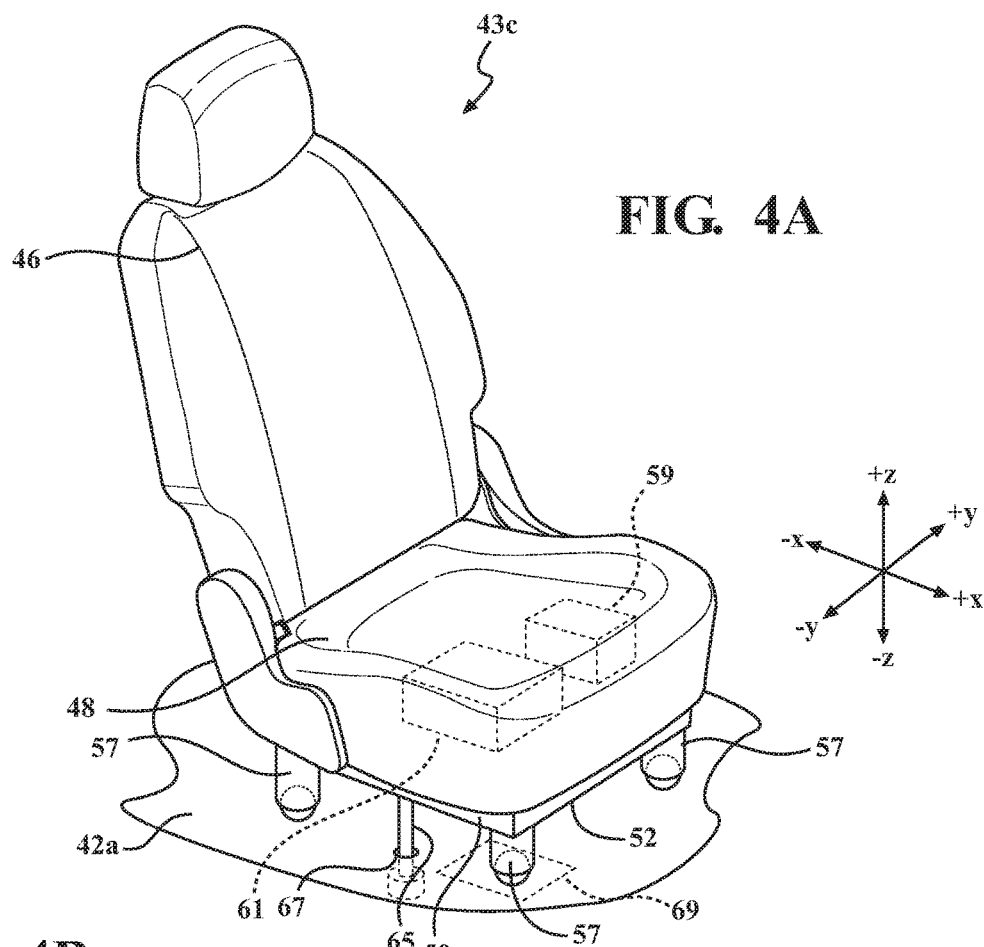
FIG. 4A schematically depicts an isolated view of a rear passenger seat with casters and a floor of the vehicle of the illustrative system of FIG. 1 according to one or more embodiments shown or described herein.
Figure 4B:
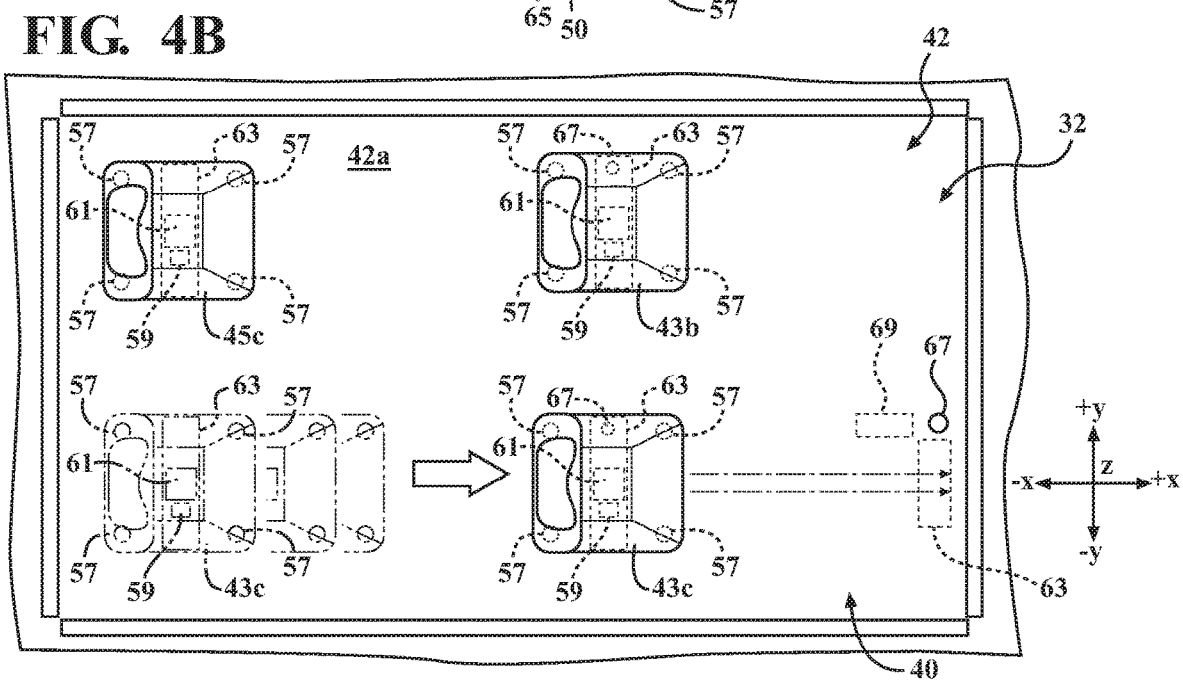
FIG. 4B schematically depicts a top view of the rear passenger seat moving across the floor of the vehicle to provide a wheelchair transportation space required for the user and the wheelchair to be positioned thereon within the vehicle according to one or more embodiments shown or described herein.
Figure 5:
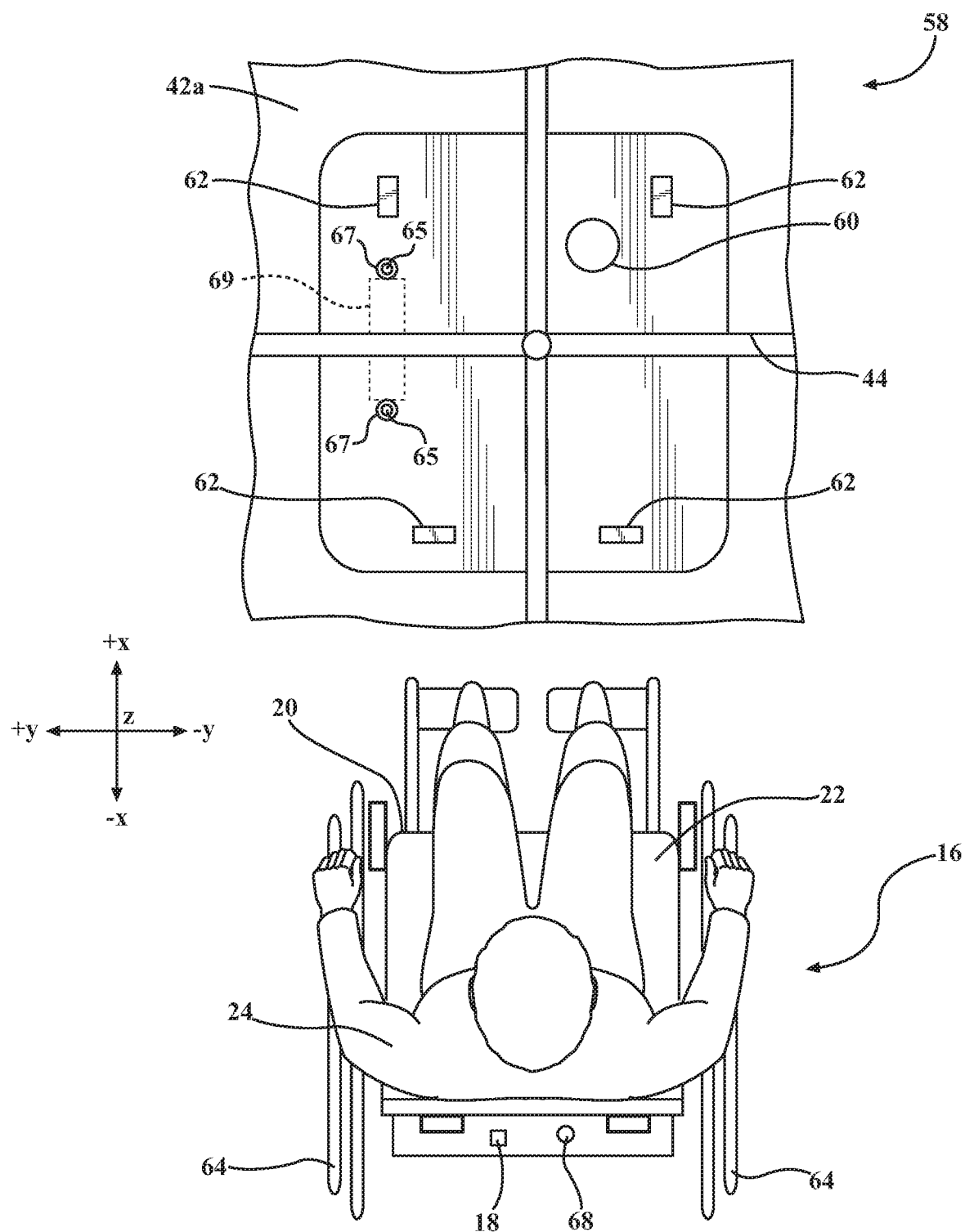
FIG. 5 schematically depicts an isolated view of the user and wheelchair and at least one docking station of FIG. 2 according to one or more embodiments shown or described herein.

Now referring to the seat 43c of FIGS. 4A-4B, while still referring to FIGS. 1-2, it should be appreciated that the seat 43c in FIGS. 4A-4B is identical to the seat 43c of FIGS. 3A-3B except as noted herein. Further, the master controller 14 and the data transmitted and gathered with respect to the seat 43c in FIGS. 4A-4B similar to that of the seat 43c in FIGS. 3A-3B and described with reference to FIG. 6, as discussed in greater detail herein.

In this embodiment, the seat 43c includes at least one actuator 59 communicatively coupled to the master controller 14 of the example vehicle 12, similar to the at least one actuator 56 as described with respect to FIGS. 3A-3B. In other embodiments, the at least one actuator 59 is positioned below the floor surface 42a in the system vertical direction (i.e., in the +/−Z direction) and is communicatively coupled to the master controller 14 of the example vehicle 12.

Each of the plurality of casters 57 is positioned so to make contact with the floor surface 42a of the floor 42. In some embodiments, each of the casters of the plurality of casters 57 is a roller, a wheel, and the like. Each of the plurality of casters 57 are configured to swivel and direct movement of each seat of the plurality of rear passenger seats 40 in 360 degrees. In some embodiments, a seat sensor 61 may be positioned in each seat of the plurality of rear passenger seats 40 and a floor sensor 63 may be positioned below the floor surface 42a in the system vertical direction (i.e., in the +/−Z direction). In some embodiments, the seat sensor 61 may be a plurality of sensors in which the seat sensor 61 may be a magnet, a radio frequency indemnification (RFID) transmitter or receiver, an infrared sensor, a proximately sensor, a laser sensor, and the like. Further, in some embodiments, the floor sensor 63 may be a plurality of sensors. The floor sensor 63 may be a magnet, a radio frequency indemnification (RFID) transmitter or receiver, an infrared sensor, a proximately sensor, a laser sensor, and the like, that corresponds to each seat sensor 61 is selectively communicatively coupled to each seat sensor 61, and the like. As such, the floor sensor 63 may be positioned at the locations where the each seat of the plurality of rear passenger seats 40 may be positioned within the rear passenger area 32 of the example vehicle 12. In some embodiments, each one of the seat and floor sensors 61, 63 may be electromagnetic, electric, magnetic, and the like, as discussed herein, and are each communicatively coupled to the master controller 14 to selectively activate and deactivate each one of the seat and floor sensors 61, 63. In operation, when one of the seat and floor sensors 61, 63 are each activated, the seat 43c, via the plurality of casters 57, may be driven or moved across the floor surface 42a such that the seat 43c moves to the desired position within the rear passenger area 32.

In other embodiments, each one of the seat sensors 61 may be coupled to the at least one actuator 59 which may selectively engage the seat sensor 61 to activate that particular seat sensor 61. In yet other embodiments, at least one second actuator 69 may be positioned below the floor surface in the system vertical direction (i.e., in the +/−Z direction). The at least one second actuator 69 may be configured to selectively energize or activate at least one of the floor sensors 63 and/or that may be configured to move the floor sensor 63 to a desired seat position within the rear passenger area 32 and then energizes or activates the floor sensor 63. In response, the master controller 14 energizes or activates the seat sensor 61 in the seat 43c such that the seat moves, via the plurality of casters 57, across the floor surface 42a into the desired position within the rear passenger area 32.

Once the seat 43c is within the desired position within the rear passenger area 32, in some embodiments, at least one locking mechanism 65 may extend through at least one aperture 67 in the floor surface 42a. That is, each one of the at least one locking mechanism 65 may extend through a corresponding at least one aperture 67. The at least one locking mechanism 65 may be actuator driven and may be configured to engage with the bottom surface 52 of the seat frame 50 to prevent the seat 43c from unwanted movement across the floor 42. In some embodiments, the at least one second actuator 69 is configured to actuate the at least one locking mechanism 65. Further, in some embodiments, there may be more than one of the at least one locking mechanism 65 coupled to the at least one second actuator 69. In other embodiments, the at least one locking mechanism 65 may be coupled to the seat frame 50, similar to the at least one track engagement member 54. In this embodiment, once the seat 43c is within the desired position within the rear passenger area 32, the at least one locking mechanism 65 may be extended, via the at least one actuator 56 (FIG. 3A) from the seat frame 50 through the at least one aperture 67 of the floor surface 42a. As such, it should be understood that the at least one locking mechanism 65 may be actuator driven from either beneath the floor surface 42a or from the seat frame 50 and may be configured to engage with a side edge of the at least one aperture 67 of the floor 42 and the at least one actuator 56 to prevent the seat 43c from unwanted movement across the floor 42.

Now referring to FIGS. 1-5, the floor 42 may also have at least one docking station 58. The at least one docking station 58 may be disposed below the at least one of the plurality of rear passenger seats 40, such as the second row third seat 43c, in the system vertical direction (i.e., in the +/−Z direction). As such, when the seat 43c moves, or any other of the plurality of rear passenger seats 40 moves, the at least one docking station 58 may be accessible to the wheelchair 16 and the user 24. The at least one docking station 58 is configured to communicatively couple the wheelchair 16 to the example vehicle 12 via a communication hub 60. In some embodiments, the at least one docking station 58 may further include at least one recess 62 configured to receive at least one wheel 64 of the wheelchair 16 such that the wheelchair 16 is secured to the vehicle during transportation. Further, it should be appreciated that the example vehicle 12 and/or the at least one docking station 58 may further include straps, belts and the like to assist in securing the wheelchair 16 to the at least one docking station 58 during transportation. In other embodiments, the at least one docking station 58 includes the at least one aperture 67 and the at least one locking mechanism 65 positioned below the floor surface 42a in the system vertical direction (i.e., in the +/−Z direction). The at least one locking mechanism 65 is configured to extend upwardly and connect to the power base portion 20 of the wheelchair 16 to secure the wheelchair 16 into the at least one docking station 58 and communicatively coupled to the communication hub 60.

The communication hub 60 may be configured to communicatively couple the master controller 14 and other vehicle components, such as a vehicle battery 66. Further, the communication hub 60 may be configured to communicatively couple to the control unit 18 and other components of the wheelchair 16, such as a wheelchair battery 68. As such, the communication hub 60 may be configured to charge the wheelchair battery 68 of the wheelchair 16 based on a transmitted data, for example, state of charge, destination, tasks after reaching the destination, and the like, such that the master controller 14 of the example vehicle 12 determines a required reserve charge level for the wheelchair 16 and delivers the charge, as discussed in greater detail herein. In some embodiments, it should be appreciated that the communication hub 60 may be communicatively coupled to the master controller 14 and other vehicle components, such as a vehicle battery 66 and/or to the control unit 18 and other components of the wheelchair 16, such as a wheelchair battery 68 either wired and/or wirelessly.

It should be appreciated that the reserve charge level calculation may incorporate terrain conditions at the requested destination of the user 24 that impact charging levels, (e.g., hill grade, regen opportunities, and the like). Further, it should also be appreciated that the charging rate may vary depending on the amount of charge required (i.e., fast charging, normal charging, and maintenance charging), the amount of time before reaching the destination, the type of the wheelchair battery 68, and the like. It should be also appreciated that a type of charge may vary between the at least one docking station 58. That is, one of the at least one docking station 58 may provide an alternating current (AC) charge while another provides a direct current (DC) charge. The communication hub 60 of the at least one docking station 58 may be bidirectional such that the wheelchair 16 may share the charge of the wheelchair battery 68 with the example vehicle 12 in case of a low vehicle charge condition.

The master controller 14 may generally be a standalone control device that contains one or more components for controlling movement of the plurality of rear passenger seats 40, and the on board vehicle components such as the at least one docking station 58 the communication hub 60, the vehicle battery 66 and the like. Further, in some embodiments, when the wheelchair 16 is docked to the at least one docking station 58 and communicatively coupled to the communication hub 60, the master controller 14 may also control the wheelchair 16 and component thereof. It should be appreciated that while the master controller 14 is shown in FIGS. 1-2 as part of the example vehicle 12, this is a non-limiting example. That is, the master controller 14 may be a device that is separate from the example vehicle 12, such as a device that is coupled to or integrated with the wheelchair 16. In some embodiments, the master controller 14 may be separate from both the wheelchair 16 and the example vehicle 12, such as, for example, a user carried computing device, the user's mobile device, or the like.

Figure 6:
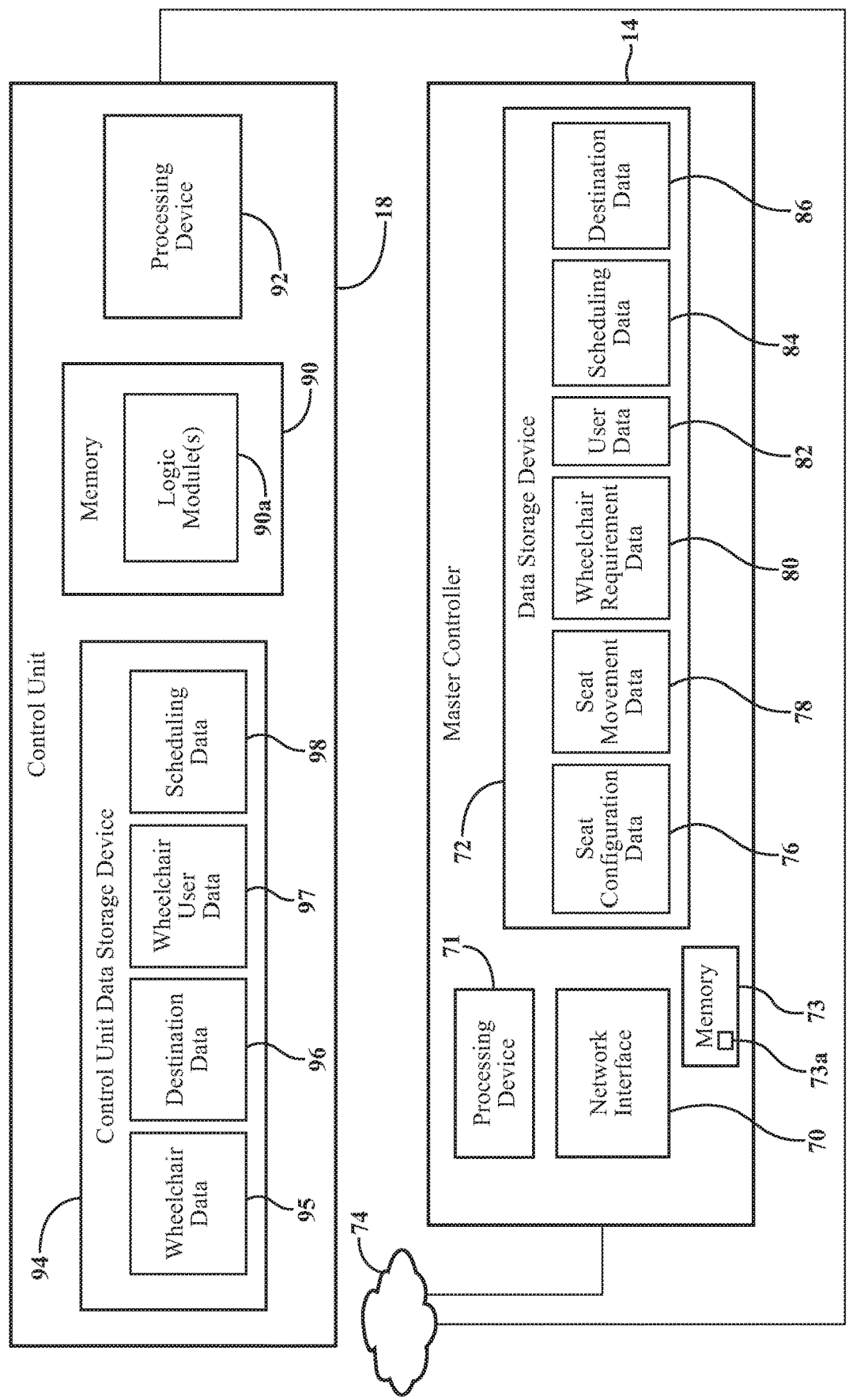
FIG. 6 schematically depicts a block diagram of illustrative components of a communication system according to one or more embodiments shown or described herein.

FIG. 6 depicts various illustrative internal components of the master controller 14 and internal components of the control unit 18 communicatively coupled together according to embodiments. More specifically, the master controller 14 may be communicatively coupled to the control unit 18 via a network 74. The network 74 may include a wide area network (WAN), such as the Internet, a local area network (LAN), a mobile communications network, a public service telephone network (PSTN), a personal area network (PAN), a metropolitan area network (MAN), a virtual private network (VPN), a Bluetooth connection, and/or another network that can electronically connect to the master controller 14 and the control unit 18 together.

In various embodiments, the control unit 18 may include, but is not limited to, a memory component 90 and a processing device 92. The processing device 92, such as a computer processing unit (CPU), may be the central processing unit of the control unit 18, performing calculations and logic operations to execute a program. The processing device 92, alone or in conjunction with the other components, is an illustrative processing device, computing device, processor, or combination thereof. The processing device 92 may include any processing component configured to receive and execute instructions (such as from the memory component 90).

In some embodiments, the memory component 90 may be configured as a volatile and/or a nonvolatile computer-readable medium and, as such, may include random access memory (including SRAM, DRAM, and/or other types of random access memory), read only memory (ROM), flash memory, registers, compact discs (CD), digital versatile discs (DVD), and/or other types of storage components. Further, the memory component 90 may be a non-transitory, processor-readable memory. The memory component 90 may include one or more programming instructions thereon that, when executed by the processing device 92, cause the processing device 92 to complete various processes, such as one or more of the processes described herein with respect to FIGS. 7-9.

Still referring to FIG. 6, the programming instructions stored on the memory component 90 may be embodied as one or more software logic modules 90a, where each logic module 90a provides programming instructions for completing one or more tasks, as described in greater detail below with respect to FIGS. 7-9. Still referring to FIG. 6, the logic module 90a includes a plurality of different pieces of logic, each of which may be embodied as a computer program, firmware, and/or software/hardware, which may be executable by the processing device 92.

The control unit 18 further includes a control unit data storage device 94, which may generally be a storage medium, may contain one or more data repositories for storing data that is received and/or generated. The control unit data storage device 94 may be any physical storage medium, including, but not limited to, a hard disk drive (HDD), memory, removable storage, and/or the like. While the control unit data storage device 94 is depicted as a local device, it should be understood that the control unit data storage device 94 may be a remote storage device, such as, for example, a server computing device or the like. Illustrative data that may be contained within the control unit data storage device 94 is described below with respect to FIGS. 7-9 and includes, but is not limited to, a wheelchair data 95, a destination data 96, a wheelchair user data 97 and a wheelchair scheduling data 98.

The control unit data storage device 94 stores the data that may be input by the user 24, the manufacturer of the wheelchair, a third party, and the like. As such, the user may program destination data, biometric data, scheduling data, tasks after reaching destination and the like. This data may be programmed directly into the control unit 18, via a laptop or other personal electronic device such as a tablet, via an application on a mobile electronic device, such as a smart phone, and the like.

In particular, the wheelchair data 95 may contain data relating to wheelchair requirements such as size, weight, wheelchair turning radius, and the like, wheelchair battery state of charge, and the like. The destination data 96 may be data relating to wheelchair destination information, wheelchair tasks preformed at the destination, and the like. The wheelchair user data 97 may contain data relating to the biometric identification, which may include data related to user-specific variables such as weight, height, disabilities, and the like. The wheelchair scheduling data 98 may be data relating to reservations and/or appointments, which may be cloud-based, and incorporate variable loading and/or unloading times to maintain scheduled reservation and/or appointment times. It should be appreciated that some data may not be transmitted until the wheelchair is docked into the at least one docking station and is communicatively coupled to the communication hub 60. For example, the battery state of charge may be accessed after docking.

In various embodiments, the master controller 14 includes a network interface 70, a processing device 71, a data storage device 72, and a memory 73. The processing device 71, such as a computer processing unit (CPU), may be the central processing unit of the master controller 14, performing calculations and logic operations to execute a program. The processing device 71, alone or in conjunction with the other components, is an illustrative processing device, computing device, processor, or combination thereof. The processing device 71 may include any processing component configured to receive and execute instructions (such as from the memory component 73).

In some embodiments, the memory component 73 may be configured as a volatile and/or a nonvolatile computer-readable medium and, as such, may include random access memory (including SRAM, DRAM, and/or other types of random access memory), read only memory (ROM), flash memory, registers, compact discs (CD), digital versatile discs (DVD), and/or other types of storage components. Further, the memory component 73 may be a non-transitory, processor-readable memory. The memory component 73 may include one or more programming instructions thereon that, when executed by the processing device 71, cause the processing device 71 to complete various processes, such as one or more of the processes described herein with respect to FIGS. 7-9.

Still referring to FIG. 6, the programming instructions stored on the memory component 73 may be embodied as one or more software logic modules 73a, where each logic module 73a provides programming instructions for completing one or more tasks, as described in greater detail below with respect to FIGS. 7-9. Still referring to FIG. 6, the logic module 73a includes a plurality of different pieces of logic, each of which may be embodied as a computer program, firmware, and/or software/hardware, which may be executable by the processing device 71.

The network interface 70 of the master controller 14 may include any wired or wireless networking hardware, such as a modem, LAN port, wireless fidelity (WiFi) card, WiMax card, mobile communications hardware, Bluetooth communications, and/or other hardware for communicating with other networks and/or devices. Therefore, the communication between the master controller 14, the at least one actuator 56 of the plurality of rear passenger seats 40, the at least one docking station 58, and/or the wheelchair 16 may be provided through the network interface 70. In one example, the master controller 14 may wirelessly communicate with the at least one actuator 56 of the plurality of rear passenger seats 40 and the wheelchair 16.

It should be appreciated that the automatic interior seat movement and/or configurations of the plurality of rear passenger seats 40, as discussed in greater detail herein, may be transmitted to the master controller 14 through the network interface 70. Further, it should be appreciated that the user 24 may select the automatic interior seat movement and/or configurations of the plurality of rear passenger seats 40 by voice control, voice activation, a push button or from a program selection initiated at an external device from the master controller 14 such as a portable computing device, smartphone, or the like, or from the wheelchair 16.

The data storage device 72, which may generally be a storage medium, may contain one or more data repositories for storing data that is received and/or generated. The data storage device 72 may be any physical storage medium, including, but not limited to, a hard disk drive (HDD), memory, removable storage, and/or the like. While the data storage device 72 is depicted as a local device, it should be understood that the data storage device 72 may be a remote storage device, such as, for example, a server computing device or the like. Illustrative data that may be contained within the data storage device 72 is described below with respect to FIGS. 6-7 and includes, but is not limited to, a seat configuration data 76, a seat movement data 78, a wheelchair requirement data 80, a user data 82 that may generated by the user 24, a scheduling data 84, and a destination data 86.

The data storage device 72 stores the data as received from the control unit 18 from the wheelchair 16 and from the master controller 14, as discussed herein. The master controller 14 may utilize the data within the data storage device 72 from the seat configuration data 76, the seat movement data 78, the wheelchair requirement data 80, the user data 82, the scheduling data 84, the destination data 86, and so on, to coordinate a movement, multiple movements, or resolve a conflict between the various seats of the plurality of rear passenger seats 40, (FIGS. 1-2) as discussed in greater detail herein.

Referring also to FIGS. 1-2, the control unit 18 of the wheelchair 16 may transmit data to the master controller 14 related to a biometric identification of the user, parameters for automatic vehicle seat adjustments, wheelchair battery state of charge, destination information of the wheelchair and/or user, tasks to be performed after reaching the destination, special needs, scheduling information, and the like. In particular, the seat configuration data 76 may contain data relating to optimal seat configuration based on various other data, such as the wheelchair requirement data 80, the user data 82, and the like. The seat movement data 78 may contain data relating to current seat configuration, actuator location data, current passenger location, current wheelchair and user data, and the like. The user data 82 may contain data relating to the biometric identification, which may include data related to user-specific variables such as weight, height, disabilities, and the like. The wheelchair requirement data 80 may contain data relating to wheelchair requirements such as size, weight, wheelchair turning radius, and the like, wheelchair battery state of charge, and the like. The scheduling data 84 may be data relating to reservations and/or appointments, which may be cloud-based, and incorporate variable loading and/or unloading times to maintain scheduled reservation and/or appointment times. The routes taken by the vehicle may be modifiable in support of the reservation and/or appointment timing. The destination data 86 may be data relating to wheelchair destination information, wheelchair tasks preformed at the destination, and the like.

As such, the parameters for automatic vehicle seat adjustments may be a combination of data from the seat configuration data 76, the seat movement data 78, the wheelchair requirement data 80, the user data 82, the scheduling data 84, and/or the destination data 86. Therefore, the data storage device 72 may receive this data from the control unit 18, from the master controller 14 and the like, and store this data as the data in the seat configuration data 76, the seat movement data 78, the wheelchair requirement data 80 the user data 82, the scheduling data 84, the destination data 86. The master controller 14, based at least in part of the data stored in the data storage device 72, may determine the rear seat configuration and automatic movement of the plurality of rear passenger seats 40, the placement of the wheelchair 16, the user 24, the wheelchairs and/or users already within the passenger compartment 26 of the example vehicle 12, and the like, and in turn transmit a signal to at least one actuator 56 to cause the plurality of rear passenger seats 40 to move into the determined configuration. It should be appreciated that the determined seat configuration may automatically move current wheelchairs and/or users on other docking stations and/or other passengers already seated on the plurality of rear passenger seats 40 to obtain the optimum configuration based on the biometric identification of the user, parameters for automatic vehicle seat adjustments, wheelchair battery state of charge, destination information of the wheelchair and/or user, tasks to be performed after reaching the destination, special needs, scheduling information, and the like.

In some embodiments, under one operation, the current wheelchairs and/or users may move independently of the plurality of rear passenger seats 40 such that the optimal seat configuration may be obtained. As such, the seat configuration may be predetermined logic programs that are stored in the logic module 73a and initiated during independent operation of the example vehicle 12 and the wheelchair 16 when the wheelchair 16 is within range to communicate with the master controller 14. Under another operation, a program stored in the logic module 73a may be accessed and executed whereby the master controller 14 may coordinate the movements of the plurality of rear passenger seats 40 to achieve a particular function, movement, and/or the like, such as providing an optimal seat configuration based on the user 24 biometric identification data and the requirements of the wheelchair 16. In some embodiments, the operations may be completed on the fly (i.e., as the user actively arrives at the example vehicle 12 for pickup) or may be completed as a preset program (i.e., prescheduled, predetermined, and/or the like).

In some embodiments, during coordinated movement of the plurality of rear passenger seats 40, the master controller 14 may monitor and may refer to the seat configuration data 76, the seat movement data 78, the wheelchair requirement data 80 the user data 82, the scheduling data 84, and/or the destination data 86 to determine a position, an orientation, and/or the like each seat of the plurality of rear passenger seats 40, passengers of the example vehicle 12, other wheelchairs and/or user of the example vehicle 12, and the like, as discussed herein. As such, the master controller 14 may then concurrently provide instruction signals to the at least one actuator 56 to move the respective seats of the plurality of rear passenger seats 40, the respective passengers, other wheelchairs and/or users as appropriate.

It should be understood that while some of the components of FIG. 6 are illustrated as residing within the master controller 14 while others reside within the control unit 18, this is merely an example thereof. In some embodiments, one or more of the components may reside solely within the master controller 14, or, in the alternative, one or more components may be external to the control unit 18 and to the master controller 14.

It should also be appreciated that the master controller 14 may receive new and/or updated instructions or configurations as needed. It should also be appreciated that the logic module 73a, the memory component 73 and/or the processing device 71 may also receive updates and/or new seating configurations, programs, and the like, from time to time. These updates may be based on the new biometric information of users, new types of wheelchairs, different requirements for wheelchairs, and the like.

Figure 7:
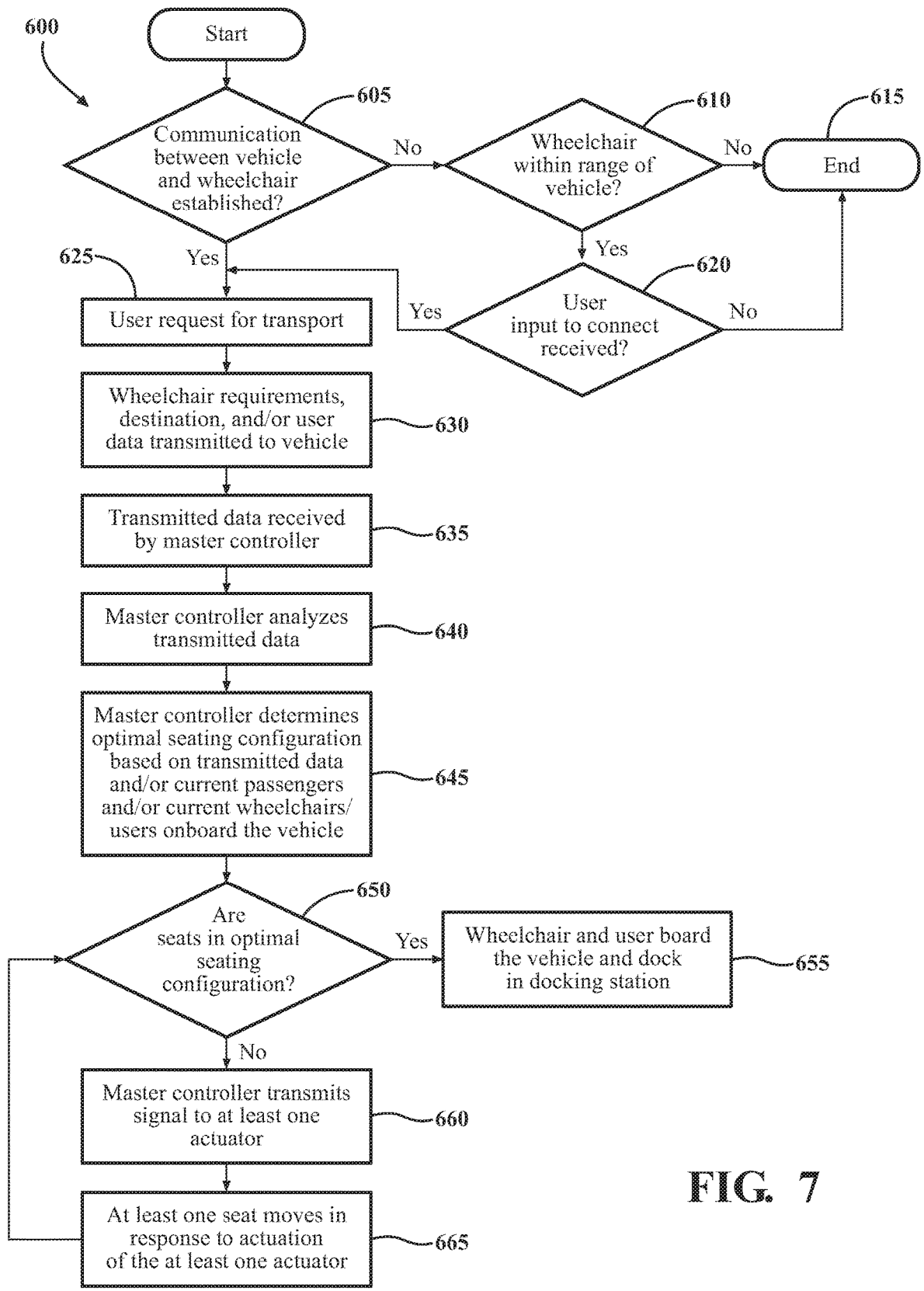
FIG. 7 depicts a flowchart of an illustrative method of communication between the master controller and the wheelchair of the illustrative system of FIG. 1 according to one or more embodiments shown or described herein.

Now referring to FIG. 7, a flowchart of an illustrative method 600 of communication between the master controller and the wheelchair of FIGS. 1-2 is depicted. In some embodiments, the master controller may be in continuous communication with the wheelchair to execute the various steps depicted in FIG. 6 and is limited only by the type of networking hardware used to communicatively couple the wheelchair to the vehicle. For example, WIFi and Bluetooth may only work when the wheelchair is connected to the network via a user input, a distance between the vehicle and the wheelchair, and the like. As such, the master controller is constantly monitoring for a communication to the wheelchair to be established, at block 605. If there is not an established communication, then, at block 610, it is determined whether the wheelchair is within range of the vehicle. That is, is the wheelchair within range of the vehicle to use WIFi, Bluetooth, or the like to communicatively couple the wheelchair to the master controller.

If the wheelchair is not within range of the master controller, the method ends at block 615. If the wheelchair is within range of the master controller, the system monitors for a user input to connect, at block 620. If a user input to communicate is not received, the method ends at block 615. If the user input to connect is received at block 620, then the system determines that communication between the master controller and the wheelchair is established, at block 610. At block 625, the system monitors for a user request to transport. Once the user request for transport is initiated, the wheelchair requirements, destination data, and/or user data is transmitted to the vehicle, at block 630, via communication between the control unit and the master controller.

Then, at block 635, the transmitted data is received by the master controller. The master controller analyzes the data, at block 640, and then determines the optimal seating configuration based on the transmitted data and/or based on the current passengers and/or current wheelchairs/user within the vehicle. That is, the seating arrangement of the current passengers, the current wheelchairs/users, each of their placement within the plurality of rear passenger seats and their destinations may impact the optimal seating arrangement. At block 650, the system determines whether the current seating configuration is the optimal seating configuration with including the onboarding wheelchair and user. If the current seating arrangement is in the optimal seating arrangement, then the wheelchair and user boards and docks in the at least one docking station at block 655.

If the system determines that the current seating configuration is not the optimal seating configuration, at block 650, then the master controller transmits a signal to the at least one actuator, at block 660. In response, at least one seat moves, at block 665, and the system again confirms whether the current seating configuration is the optimal seating configuration, at block 650. The process 600 may further return to block 605 upon detection of a subsequent wheelchair and user. As such, it should be appreciated that the processes described with respect to FIG. 6 are arranged as a loop that continues for as long as a wheelchair and user are in communication with the vehicle and request for transporting by the vehicle.

Figure 8:
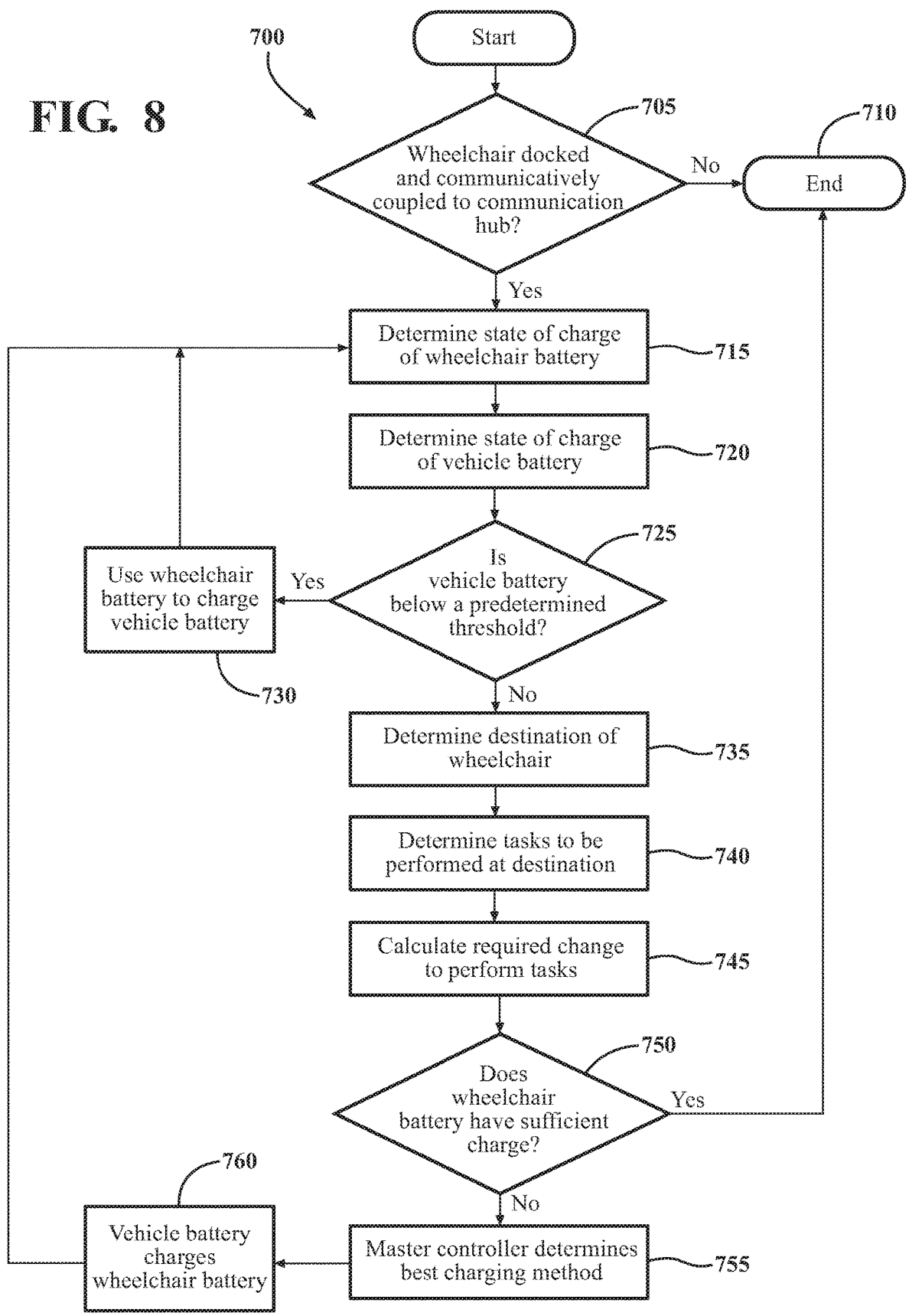
FIG. 8 depicts a flowchart of illustrative method of communication between the master controller and the wheelchair via a communication hub of FIG. 4 according to one or more embodiments shown or described herein.

Now referring to FIG. 8, a flowchart of an illustrative method 700 of communication between the master controller and the wheelchair via the communication hub of FIG. 4 is depicted. In some embodiments, the communication hub may be in continuous communication with the wheelchair to execute the various steps depicted in FIG. 7. As such, the system determines if the wheelchair is docked and communicatively coupled to the communication hub, at block 705. If there is not an established communication, then at block 710, the process ends. Once docked, the communication hub is communicatively coupled to the control unit of the wheelchair to determine a state of charge of the wheelchair battery, at block 715. The system then determines the amount of charge of the vehicle battery, at block 720. The master controller determines whether the vehicle battery is below a predetermined threshold, at block 725, and if so, uses the wheelchair battery to charge the vehicle battery, at block 730.

Then, the destination of the wheelchair is determined, at block 735, and the tasks to be determined at the destination, at block 740. The master controller calculates the amount of charge required to perform the tasks at block 745, and whether the wheelchair battery has a sufficient charge to meet the amount of charge required, at block 750. If no, the master controller then determines how best to charge the wheelchair battery, at block 755 and charges the wheelchair battery, at block 760. The determination of how to best charge the wheelchair battery may be based on whether the docking station is an AC charge station, a DC charge station, a combination thereof, time to destination, and the like. Once the wheelchair battery is charged, at block 760, or it is determined that the battery has sufficient charge, at block 750, or after the wheelchair battery is used to charge the vehicle battery, at block 730, the system monitors the state of the charge of the wheelchair battery, at block 715. The process 700 may further return to block 705 upon a subsequent wheelchair docked and communicatively coupled to the communication hub. As such, it should be appreciated that the processes described with respect to FIG. 7 are arranged as a loop that continues for as long as a wheelchair is docked and communicatively coupled to the at least one docking station.

Figure 9:
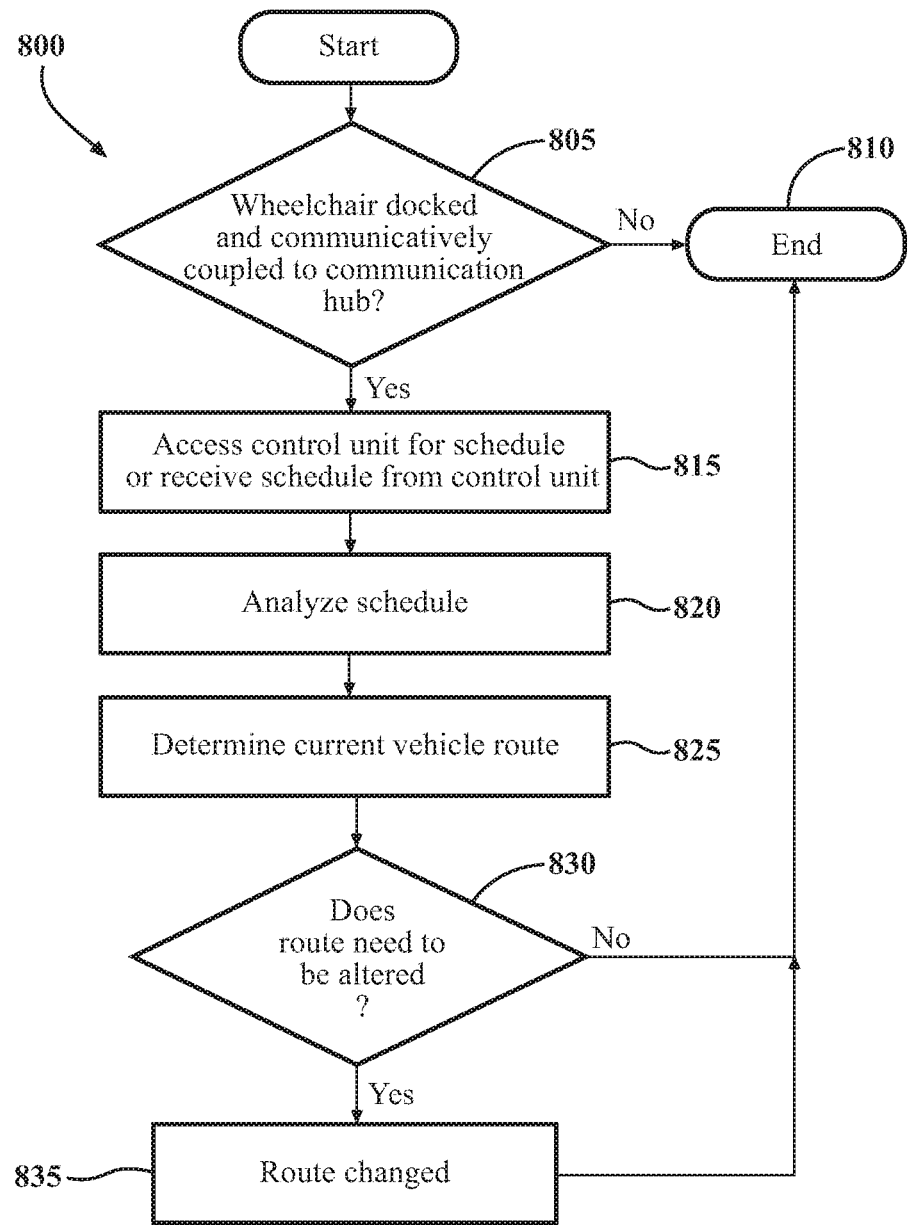
FIG. 9 depicts a flowchart of illustrative method of scheduling data communication between the master controller and the wheelchair according to one or more embodiments shown or described herein.

Now referring to FIG. 9, a flowchart of an illustrative method 800 of communication between the master controller and the wheelchair, via the communication hub of FIG. 4, which may alter the route of the vehicle, is depicted. In some embodiments, the master controller may be in continuous communication with the wheelchair to execute the various steps depicted in FIG. 8 and is limited only by the type of networking hardware used to communicatively couple the wheelchair to the vehicle. As such, the system determines if the wheelchair is docked and communicatively coupled to the communication hub, at block 805. If there is not an established communication, then at block 810, the process ends. Once docked, the communication hub is communicatively coupled to the control unit of the wheelchair to either access the control unit for schedule data and/or the communication hub and/or the master controller receives schedule data from the control unit, at block 815.

At block 820, the system analyzes the schedule data and then determines the current route of the vehicle, at block 825. It should be appreciated that the current route may be based on current passengers, current wheelchair/users, future pick up locations, future destinations, and the like. At block 830, the system determines whether the route that the vehicle is taking needs to be altered. It should be appreciated that the decision to change the route may be based on ensuring that the wheelchair/user make it to any scheduled appointments on time. If the route does not need to be altered, then the process ends at block 810. If the route should be changed, then the route is changed at block 835. It should be appreciated that, in some embodiments, the route change may be alerting a driver of the vehicle to change route. In other embodiments, the route change may be accomplished by sending coordinates to the vehicle and, in particular, to a GPS unit whether carried by the driver (i.e., personal electronic device) or integrated in a heads up display within the vehicle. In another embodiment, the vehicle may be autonomously or semi-autonomously driven and the route change may automatically or semi-automatically divert the vehicle to the new route.

It should now be understood that the systems and methods described herein include an interface between a wheelchair and a vehicle. The vehicle is configured to transport users and wheelchairs. The vehicle is further configured to receive communications from the wheelchair and manipulate or move interior seating configurations, based on the communication from the wheelchair, to accommodate the wheelchair and/or the user. The vehicle may communicate with the wheelchair via Bluetooth, Wi-Fi, cellular frequencies and the like to communicatively couple a master controller of the vehicle with a control unit of the wheelchair to transmit data between them. The data transmitted between the vehicle and the wheelchair may be biometric ID, parameters for automatic vehicle seat adjustments, wheelchair battery state of charge, destination information, tasks to be performed after reaching the destination, special needs, and the like. The parameters for automatic vehicle seat adjustments may include user-specific variables such as weight, height, wheelchair requirements such as size, weight, wheelchair turning radius, and the like.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A vehicle comprising:
 a passenger compartment having a plurality of rear passenger seats disposed on a floor surface, each seat of the plurality of rear passenger seats configured to move along the floor surface, and
 a central processing unit configured to receive a biometric identification of a user of a wheelchair, the biometric identification of the user is transmitted from the wheelchair and is at least one from the group of a user weight, a user height, and a user disability, the central processing unit configured to direct a movement of each seat of the plurality of rear passenger seats along the floor surface, wherein in response to receiving the biometric identification of the user, the central processing unit actuates at least one actuator to move at least one of the plurality of rear passenger seats along the floor surface to provide a transportation space for the wheelchair based on the biometric identification received from the wheelchair.

2. The vehicle of claim 1, wherein the central processing unit is further configured to receive an additional data from the wheelchair, the additional data is a data of at least one from the group of a battery state of charge, a turning radius, a transportation space requirement, and a wheelchair model.

3. The vehicle of claim 1, wherein the transportation space for the wheelchair is at least one docking station, the at least one docking station comprises a communication hub configured to communicatively couple to the wheelchair when the wheelchair is docked in the at least one docking station.

4. The vehicle of claim 3, wherein when the wheelchair is communicatively coupled to the communication hub, the central processing unit receives a scheduling data from the wheelchair via the communication hub, the scheduling data includes at least one scheduled appointment for a user, the scheduling data is configured to be analyzed by the central processing unit and alter a route taken by the vehicle to transport the user to the at least one scheduled appointment on time.

5. The vehicle of claim 3, wherein when the wheelchair is communicatively coupled to the communication hub, the central processing unit receives a data from the wheelchair via the communication hub.

6. The vehicle of claim 5, wherein the data is a state of charge of a wheelchair battery, a destination of the wheelchair, or at least one task to be performed at the destination.

7. The vehicle of claim 6, wherein the state of charge of the wheelchair battery is compared with the destination or the at least one task to be completed at the destination to determine whether the wheelchair battery requires additional charging by the at least one docking station using a vehicle battery.

8. A system comprising:
   a vehicle comprising:
      a passenger compartment having a plurality of rear passenger seats and a floor, the floor includes a floor surface, each seat of the plurality of rear passenger seats moves along the floor surface, and
      a central processing unit,
      wherein:
         each seat of the plurality of rear passenger seats are communicatively coupled to the central processing unit, and
         the central processing unit is configured to actuate at least one actuator to direct a movement of at least one seat of the plurality of rear passenger seats along the floor surface to a predetermined location within the passenger compartment such that a transportation space is provided for a wheelchair based on a biometric identification of a user of the wheelchair transmitted to the central processing unit by the wheelchair.

9. The system of claim 8, wherein the central processing unit is further configured to receive a second data, the second data includes at least one from the group of a battery state of charge, a turning radius, a transportation space requirement, and a wheelchair model.

10. The system of claim 8, wherein the the biometric identification of the user is at least one from the group of a user weight, a user height, and a user disability.

11. The system of claim 8, wherein the transportation space for the wheelchair is at least one docking station, the at least one docking station comprises a communication hub configured to communicatively couple to the wheelchair when the wheelchair is docked in the at least one docking station.

12. The system of claim 11, wherein when the wheelchair is communicatively coupled to the communication hub, the central processing unit determines a state of charge of a vehicle battery and compares the state of charge to a predetermined threshold such that when the state of charge of the vehicle battery is below the predetermined threshold, a wheelchair battery is used to charge the vehicle battery via the communication hub.

13. The system of claim 11, wherein when the wheelchair is communicatively coupled to the communication hub, the central processing unit receives a data from the wheelchair via the communication hub, the data is a state of charge of a wheelchair battery, a destination of the wheelchair, or at least one task to be performed at the destination.

14. The system of claim 13, wherein the state of charge of the wheelchair battery is compared with the destination or the at least one task to be completed at the destination to determine whether the wheelchair battery requires additional charging by the at least one docking station using a vehicle battery.

15. A method of communicating between a vehicle and a wheelchair, the method comprising:
   receiving, by a central processing unit, an input from a user, the input corresponding to a request for transportation;
   receiving, by the central processing unit, a biometric identification of a user of the wheelchair transmitted from the wheelchair, the biometric identification of a user of the wheelchair is at least one data from the group of a user weight, a user height, and a user disability;
   determining, by the central processing unit, an optimal seat configuration of a plurality of rear passenger seats within the vehicle; and
   moving, by at least one actuator, at least one seat of the plurality of rear passenger seats into the optimal seat configuration based on the biometric identification of the user of the wheelchair.

16. The method of claim 15, wherein the central processing unit further receives at least one data from the group of a battery state of charge, a turning radius, a transportation space requirement, and a wheelchair model.

* * * * *

UNITED STATES PATENT AND TRADEMARK OFFICE
CERTIFICATE OF CORRECTION

PATENT NO. : 11,690,768 B2
APPLICATION NO. : 16/809680
DATED : July 4, 2023
INVENTOR(S) : Katsumi Nagata, Stephen McFarland and Jerry R. Tipper It is certified that error appears in the above-identified patent and that said Letters Patent is hereby corrected as shown below:

In the Specification

In Column 5, Line(s) 40, before "maximum", delete "an" and insert --a--, therefor.

In the Claims

In Column 18, Line(s) 6, Claim 10, delete "the the" and insert --the--, therefor.

Signed and Sealed this
Twenty-eighth Day of November, 2023

Katherine Kelly Vidal
*Director of the United States Patent and Trademark Office*